United States Patent [19]
Kuslich

[11] Patent Number: 6,056,749
[45] Date of Patent: May 2, 2000

[54] METHOD AND DEVICE FOR FIXING AND CORRECTING SPONDYLOLISTHESIS ANTERIORLY

[75] Inventor: Stephen D. Kuslich, Stillwater, Minn.

[73] Assignee: Spineology, Inc., Stillwater, Minn.

[21] Appl. No.: 09/268,226

[22] Filed: Mar. 15, 1999

[51] Int. Cl.[7] .................................................. A61F 17/56
[52] U.S. Cl. ............................ 606/61; 606/72; 606/98; 606/99; 623/17
[58] Field of Search .............................. 606/61, 72, 98, 606/99; 623/17

[56] References Cited

U.S. PATENT DOCUMENTS

| | | |
|---|---|---|
| 5,531,747 | 7/1996 | Ray . |
| 5,601,556 | 2/1997 | Pisharodi . |
| 5,800,547 | 9/1998 | Schäfer et al. . |

*Primary Examiner*—Michael Buiz
*Assistant Examiner*—Julian W. Woo
*Attorney, Agent, or Firm*—Vidas, Arrett & Steinkraus, P.A.

[57] ABSTRACT

A method and apparatus for fixation and correction of spondylolisthesis anteriorly includes a disk cage which is inserted into the space between adjacent vertebrae, a drill guide for guiding and aligning a drill bit to angle an opening anteriorly between adjacent vertebrae, a distractor for temporarily aligning the vertebrae to position a disk cage and an elongated hollow screw positioned in said drilled opening through one vertebra, said disk cage and into said adjacent vertebra.

22 Claims, 5 Drawing Sheets

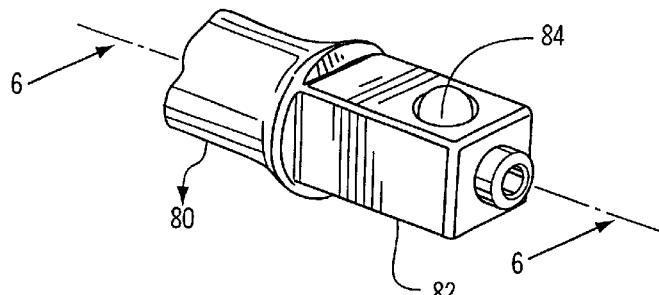
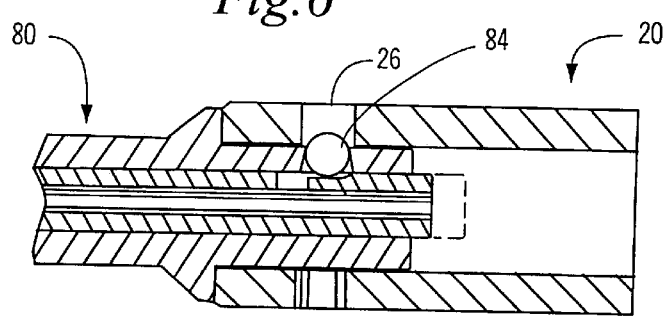
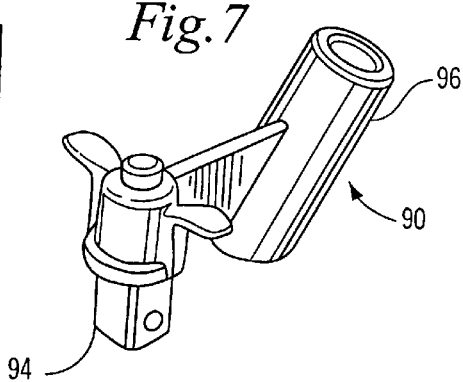
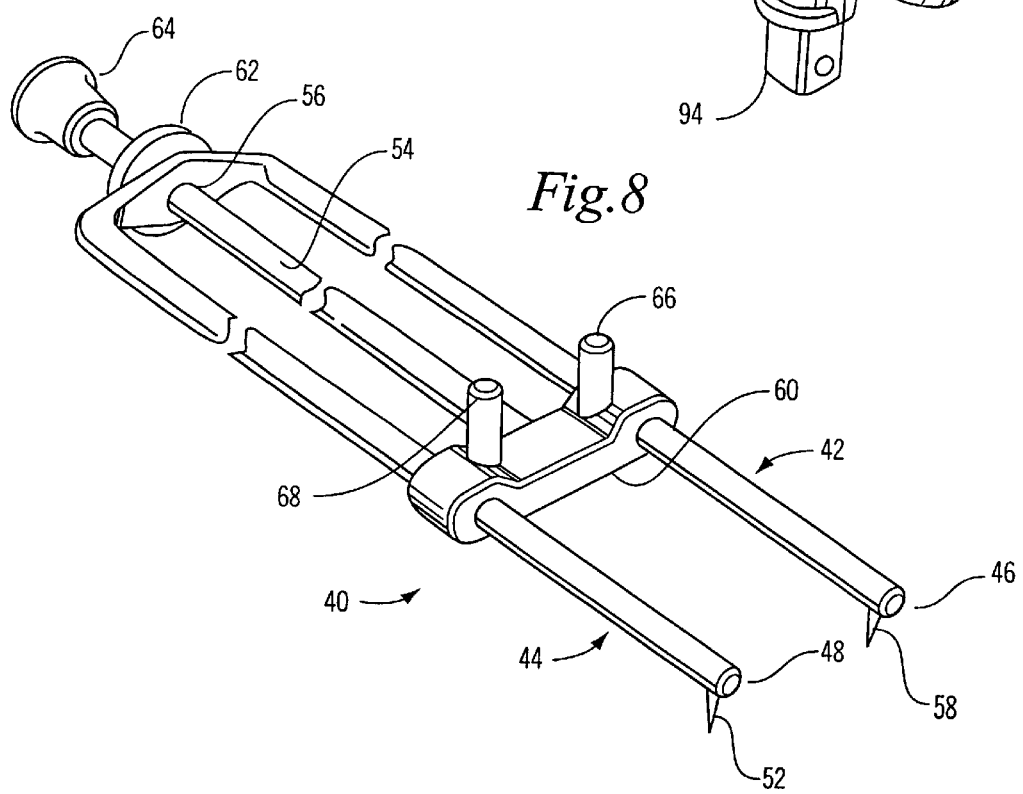

METHOD AND DEVICE FOR FIXING AND CORRECTING SPONDYLOLISTHESIS ANTERIORLY

BACKGROUND OF THE INVENTION

1. Field of the Invention

This invention relates to a method and apparatus for fixation and reduction of spondylolisthesis, e.g., misalignment of the vertebrae comprising the spinal column. More specifically, the present invention relates to a disk cage positioned in the disk space between affected vertebra, and a screw through said vertebra, disk cage and other vertebra and a method utilizing that apparatus.

2. Description of the Related Art

Treatments for conditions involving subluxation of one vertebrae upon another, resulting in misalignment of the spinal column, involve the use of screws which extend through a plate and which are tightened to draw the misaligned vertebrae back into alignment. U.S. Pat. No. 5,531,747 to Ray (hereinafter "Ray") is an example of a plate and screw system for treating spondylolisthesis. Other approaches include insertion of an implant into the disk space between misaligned vertebrae such as shown in U.S. Pat. No. 5,601,556 to Pisharodi (hereinafter "Pisharodi"). The Ray approach has its limitations as discussed in Pisharodi. That patent has a disadvantage in requiring removal of the disk and having multiple steps, that is, two implants are inserted into the disk space only to be substituted later with monolithic implants, Schäfer et al., in U.S. Pat. No. 5,800,547 discloses an angled block which is implanted into an intervertebral space. The block includes multiple openings through which securing pins extend after they are pushed into position by a camming mechanism inserted into another opening in the device.

There is, therefore, a need for an improved method of treatment of conditions involving misalignment of the vertebrae of the spinal column, or spondylolisthesis, and it is a principal object of the present invention to provide such a method and an apparatus for use in connection with that method The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

SUMMARY OF THE INVENTION

The invention provides a means for correcting and fixing spondylolisthesis anteriorly. It involves using a distracting tool against adjacent vertebra to temporarily re-align the vertebrae and to open the disk space to allow insertion of a disk cage therewithin. The disk cage is then rotated to align an angled guide hole to the adjacent vertebrae and to space the vertebrae as desired. A drill guide is placed into the disk cage to provide a guide for accurately drilling a hole through one vertebra, through the angled guide hole of the disk cage and into the adjacent vertebra. A hollow, threaded screw is then threaded into the drill hole thus formed, connecting said vertebrae together through the disk cage. The disk cage and screw may be further bonded to the fused vertebrae by application of bone ingrowth medium into the disk cage and hollow screw to allow bone and fibrous fusions to form. The implant cross-links the disk cage and screw together to stabilize the spinal motion segment.

BRIEF DESCRIPTION OF THE DRAWINGS

A detailed description of the invention is hereafter described with specific reference being made to the drawings in which:

FIG. 5 is a perspective view of the end of an insertion device for the disk cage;

FIG. 6 is a cross-sectional view of the insertion device of FIG. 5 inserted into a disk cage;

FIG. 7 is a perspective view of the screw alignment device of the invention;

FIG. 8 is a perspective view of a distracting tool for aligning adjacent vertebrae;

DESCRIPTION OF THE PREFERRED EMBODIMENTS

Figure 9:
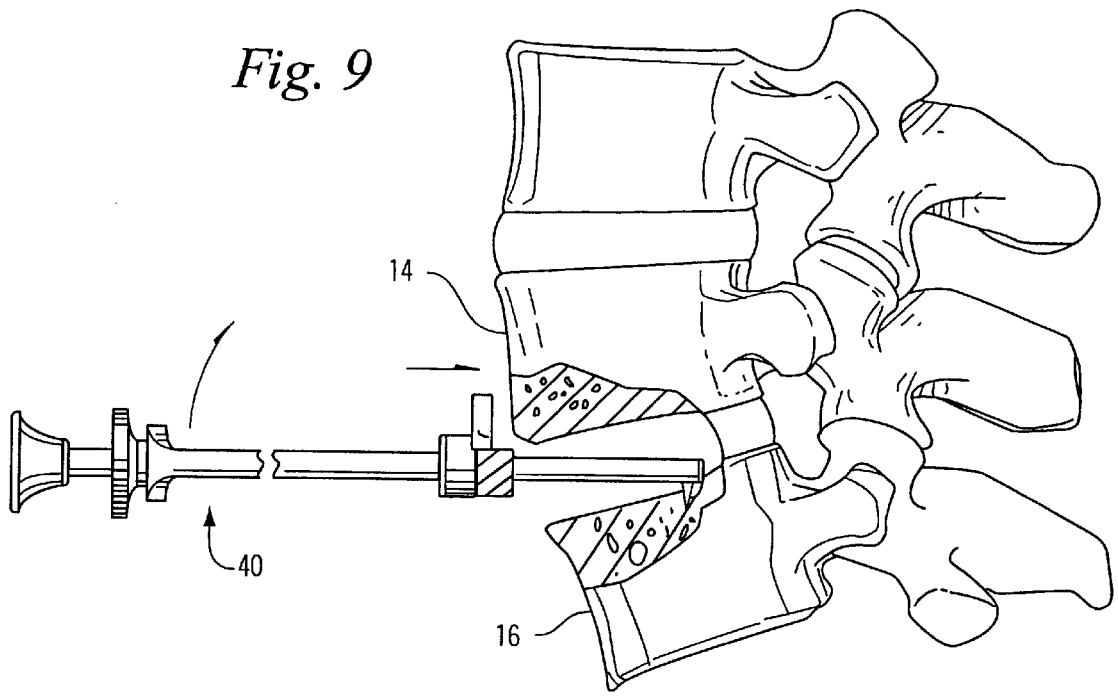
FIG. 9 shows the distracting tool being used to lift and distract one vertebra from an adjacent vertebra.

With reference to the Figures, it will be seen that a typical misalignment, or spondylolisthesis of vertebrae occurs when one vertebra slides forward relative to another as best shown in FIG. 9. Typically, the L5 vertebra is pushed anteriorly from the desired position. This causes severe pain which can be alleviated by either fixation of the vertebrae or with correction of the alignment and fixation.

Figure 1:
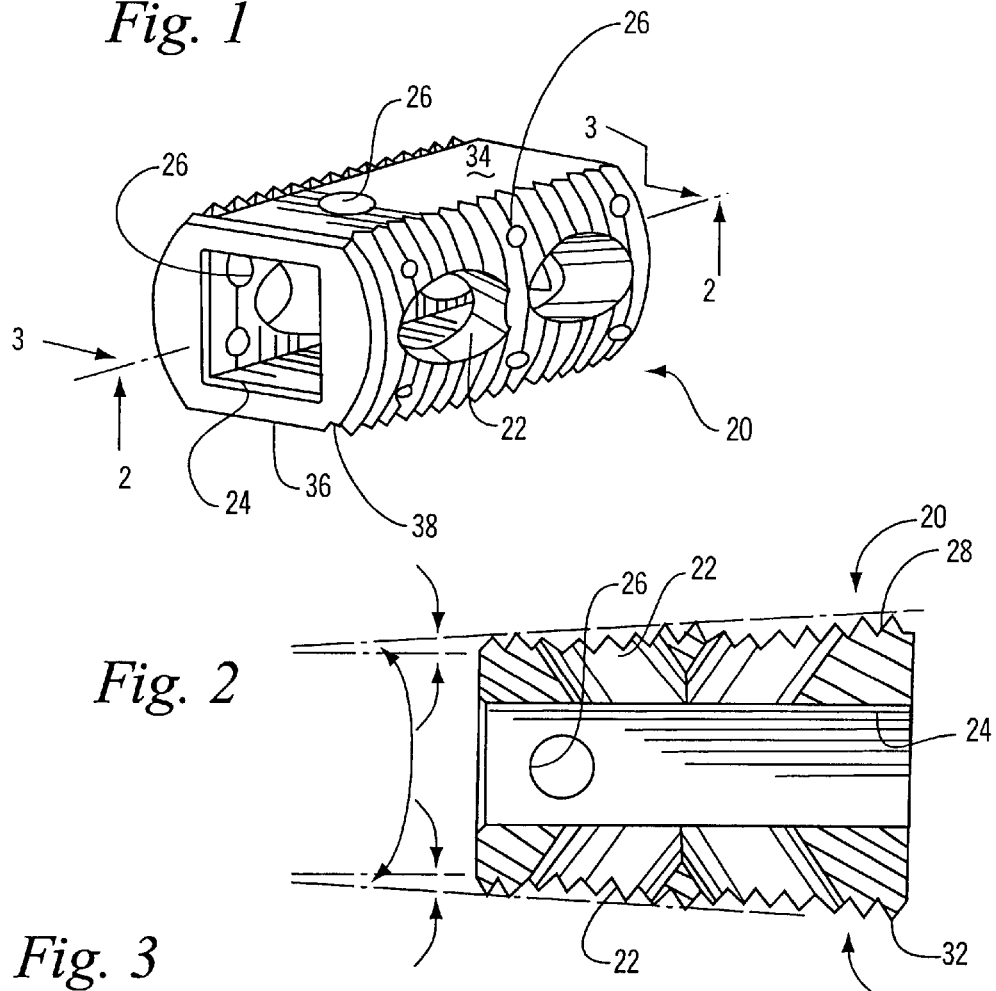
FIG. 1 is a perspective view of the disk cage of the invention.
Figure 2:
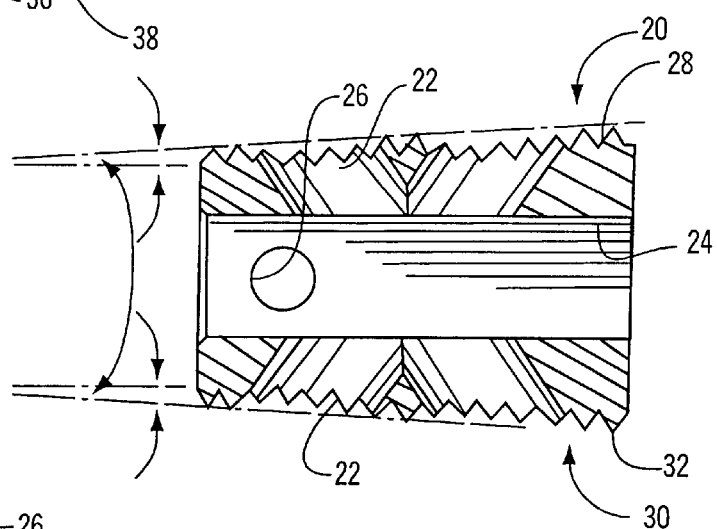
FIG. 2 is a cross-sectional view of the disk cage through line 2—2 of FIG. 1.
Figure 3:
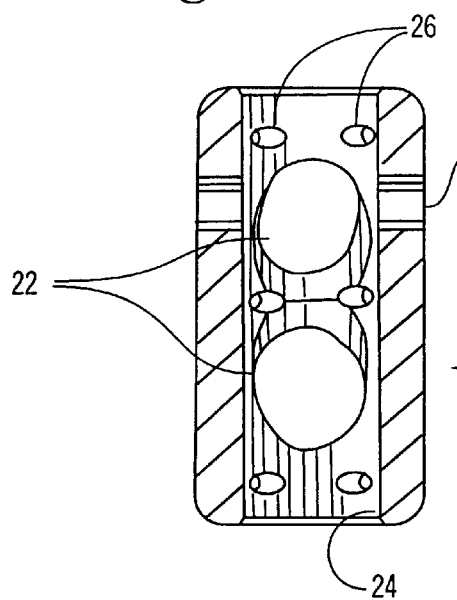
FIG. 3 is a cross-sectional view of the disk cage through line 3—3 of FIG. 1.
Figure 4:
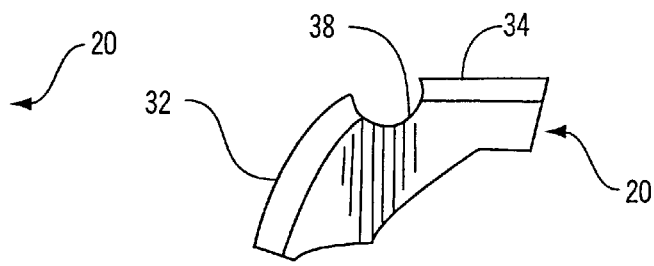
FIG. 4 is an enlarged partial view of a corner of the cage of the invention.

FIGS. 1–4 show a disk cage 20 having one or more angled guide holes 22. As shown, the disk cage 20 preferably is substantially hollow, having an opening 24 therethrough, as well as numerous side openings 26 which increase the porosity of the device such that bone ingrowth may occur. As later described, opening 24 is required to receive tool 80 and does not need to pass through cage 20. As shown, disk cage 20 includes an upper surface 28 and a lower surface 30 through which the angled guide holes 22 are positioned. In addition, surfaces 28, 30 may include threads 32 or other surface treatment to cause the surfaces to grip better to bone. FIG. 4 shows a corner of cage 20 showing that the threads 32 may stop at the intersection of the sides 34, 36 at a notch 38. Cage 20 includes a ventral end 23 and a dorsal end 25. The opening 24 which functions as the tool 80 receiving mechanism is in the ventral end 23.

Figure 10:
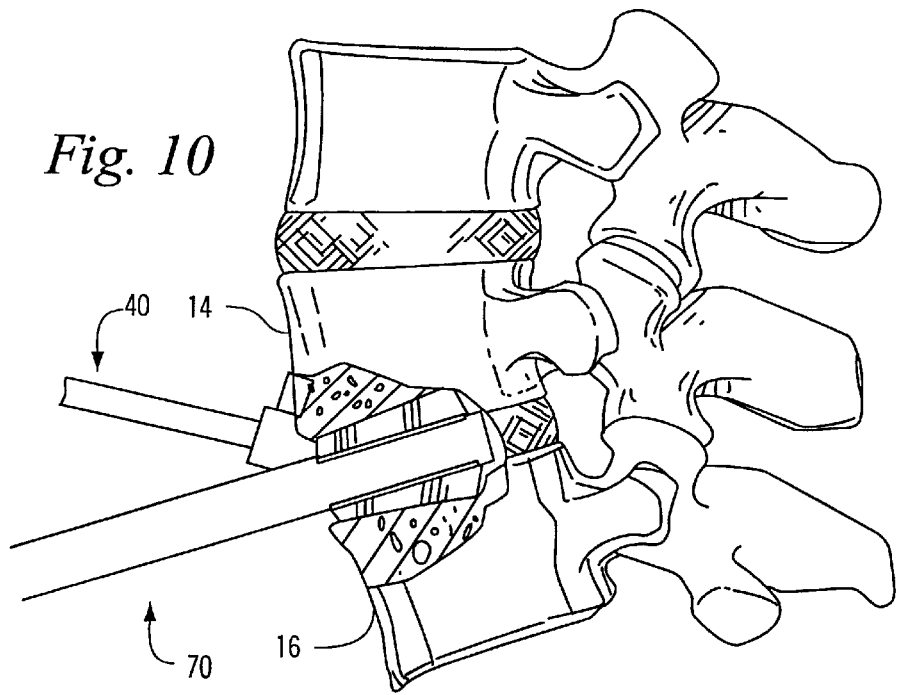
FIG. 10 shows the vertebrae properly aligned from FIG. 9 and reaming of the disk space.

In order to use the disk cage, the disk 18 must be reamed out to accommodate the size of the disk cage 20. FIGS. 8–10 show an instrument 40 used to both lift the adjacent vertebrae apart for reaming and to reduce the misalignment.

Instrument 40 includes a pair of linked arms 42, 44 having free ends 46, 48 which each include a sharp projection 50, 52 which may hold to the bone of a vertebra. Instrument 40 further includes a rod 54 attached to the linked arms 42, 44 through opening 56 and to a slide member 60 which allows the slide member 60 to move up and down along the length of the linked arms. Instrument 40 includes a depth adjustment mechanism 62 which fixes the position of the slide member 60 to the linked arms 42, 44 at the position desired. A knob 64 may be held to control the instrument during adjustment. The slide member 60 includes a pair of spaced push members 66, 68 projecting opposite to the sharp projections 50, 52.

FIG. 9 shows the instrument 40 being used to increase the gap between adjacent vertebra 14, 16 and to correct the spondylolisthesis. As shown, the instrument is inserted on either side of the disk 18 and the sharp projections 50, 52 dig into the bone of vertebra 16. The slide member 60 is adjusted down the linked arms 42, 44 by manipulating the adjustment mechanism 62 until the push members 66, 68 are firmly against the vertebra 14. The instrument 40 may then be lifted up, causing the disk space to increase and for the spondylolisthesis to be reduced. While held up, the surgeon uses a reaming tool 70 as shown in FIG. 10 to prepare the disk space for a disk cage 20. The unique configuration of instrument 40 allows the surgeon to use a reamer while the instrument distracts the vertebrae.

Figure 12:
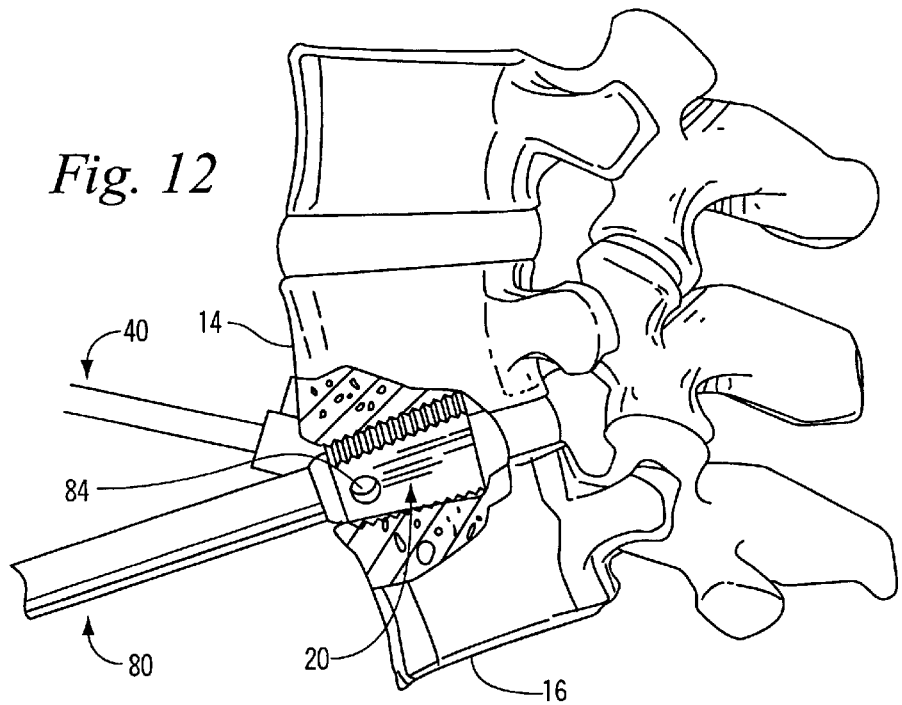
FIG. 12 shows the disk cage being inserted and rotated to align the screw holes.
Figure 13:
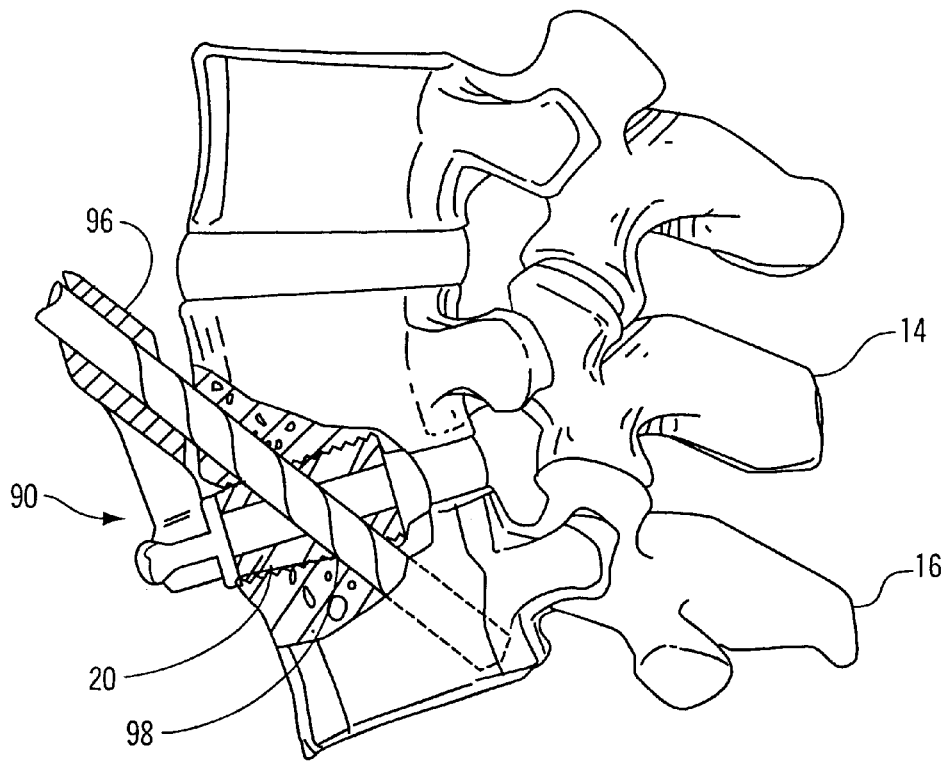
FIG. 13 shows a screw alignment device attached to a disk cage to guide a drill bit.
Figure 14:
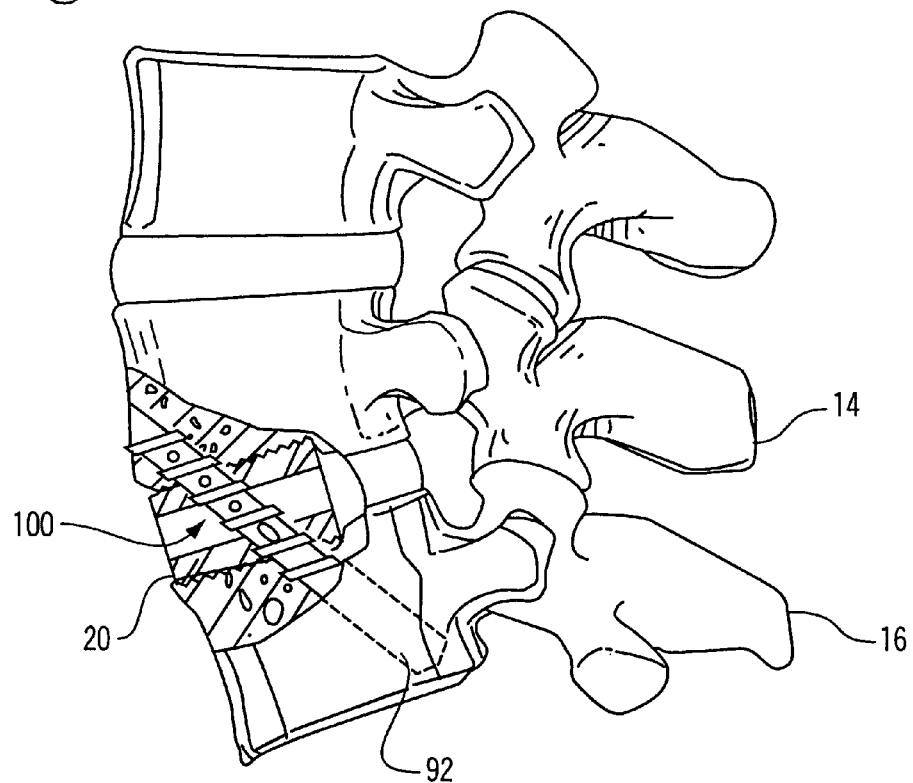
FIG. 14 shows the vertebrae held in proper alignment via a disk cage and a screw passing through a vertebra, disk cage and into the adjacent disk.

Once the disk space is prepared, the disk cage 20 is inserted. FIGS. 5, 6 and 12 show that insertion may utilize a tool 80 which includes a head 82 that may temporarily lock into opening 24 in the ventral end 23 of the disk cage 20. The tool 80 allows the surgeon to obtain leverage in inserting disk cage 20. Tool head 82 may include spring loaded, 'recessed bearings 84 which may lock into side openings 26 as is common in socket wrenches. The disk cage 20 as shown has a narrower diameter across sides 34, 36 than across upper and lower surfaces 28, 30. When so configured, the disk cage may be inserted into the disk space with a side 34, 36 up, making insertion easier. The surgeon may then simply rotate the tool 80 to twist the disk cage 20 such that the upper and lower surfaces 28, 30 engage the bone of the vertebrae and the angled guide openings 22 are positioned as shown in FIGS. 13 and 14. This allows the tool 80 to be used as a distracting tool, but the surgeon determines whether the twist is needed or whether the disk cage 20 may simply be inserted without a need for rotation.

Once in place, the disk cage is also used in conjunction with a drill guide 90 as shown in FIGS. 7 and 13 to guide the formation of a hole 92 through the vertebra 14, 16. Drill guide 90 includes a head 94 configured as head 82 to fasten to disk cage 20 and an angled guide tube 96 which is angled such that it will guide a drill bit 98 accurately through angled guide holes 22 of the disk cage 20. Hole 92 as drilled may be threaded or unthreaded. Drill guide 90 is then removed and a long, hollow screw 100 is threaded into hole 92 to fix the vertebrae 14, 16 together via the disk cage 20.

Figure 11:
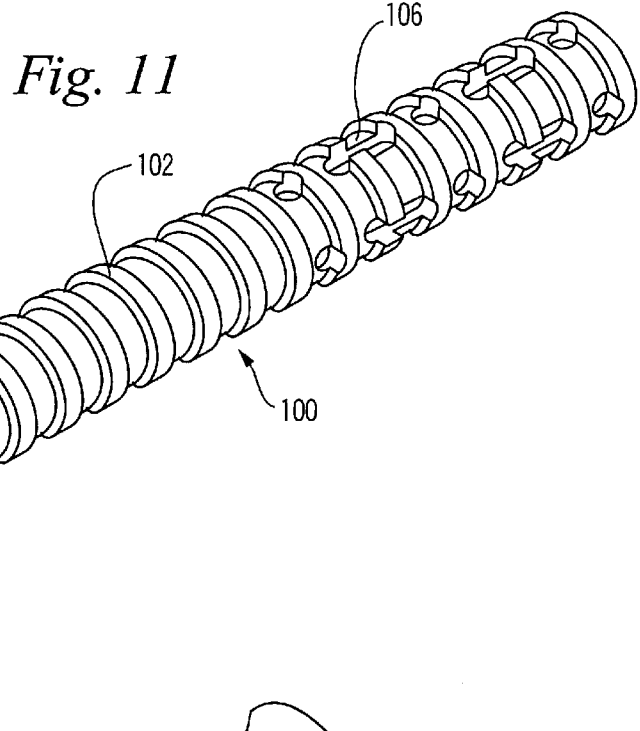
FIG. 11 shows a threaded, hollow, screw for use in securing adjacent vertebrae together through a disk cage.

As shown in FIG. 11, screw 100 is preferably hollow and includes threads 102 to engage with the bone. A variety of bone growth inducing substances may be added to the disk cage 20 and screw 100 to foster bone ingrowth therethrough to make the fusion stronger. The screw 100 as shown has a hollow bore 104 and side openings 106 for bone ingrowth.

As best shown in FIG. 14, the combination of the disk cage 20 and the screw 100 fuses the vertebrae together with very few parts in a stable, solid fusion that keeps the correction of the spondylolisthesis as desired. The tools and instruments described function to ease the insertion of the combined system which reduces and fixes the corrected alignment of the vertebrae.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. An apparatus for securing one vertebra to another in a living vertebrate animal across an interposed disk, the device including:
   (a) a rigid disk cage sized to fit within an interdiscal space to support adjacent vertebrae;
   (b) an elongated screw; and
   (c) said disk cage including an angled bore therethrough constructed and arranged such that said screw may pass therethrough such that it would enter one vertebra anteriorly, pass into said disk cage and into the adjacent vertebra to cross-pin said vertebra to said disk cage.

2. The apparatus of claim 1 wherein said disk cage is substantially hollow defining a hollow region and includes a plurality of openings from an exterior surface to the hollow region to allow bone ingrowth through said disk cage.

3. The apparatus of claim 1 wherein said disk cage includes a tool receiving mechanism for receiving an insertion and guiding tool.

4. The apparatus of claim 1 wherein said disk cage includes exterior surface treatments for gripping against a bone surface.

5. The apparatus of claim 4 wherein said disk cage is prismoidal in shape, defining six surfaces; a top and bottom surface, a right and left surface and a front and back end surface.

6. The apparatus of claim 5 wherein the distance between said top and bottom surface is greater than the distance between said right and left surfaces.

7. The apparatus of claim 6 wherein said top and bottom surfaces are generally convex and include a plurality of threads thereon.

8. The apparatus of claim 7 wherein said top and bottom surfaces are not parallel to each other.

9. Apparatus for aligning and fixing adjacent vertebrae comprising:
   (a) a disk cage having six external surface areas including a first pair of opposing generally flat exterior surfaces, a second pair of opposing generally flat exterior surfaces and a third pair of opposing surfaces defining two generally convex surfaces;
   (b) said first pair of opposing surfaces including an opening into which a tool may be inserted and held to insert and rotate the disk cage relative to a tool;
   (c) said second pair of opposing surfaces being spaced closer together than said third pair of opposing surface;
   (d) said third pair of opposing surfaces including at least one opening therethrough angling from one convex surface to the other convex surface, each of said convex surfaces including bone engagement members; and
   (e) an elongated screw sized to pass into said angled opening such that a portion of said screw extends past each convex surface in order to engage with vertebral bone when positioned within a disk and adjacent vertebrae.

10. An apparatus for securing one vertebra to another in a living vertebrate animal across an interposed disk, the device including:

(a) a rigid disk cage sized to fit within an interdiscal space to support adjacent vertebrae, said cage including an upper and a lower surface, a pair of opposing sides and a ventral and dorsal end;

(b) an elongated screw; and (c) said disk cage including an angled bore through said upper and lower surfaces constructed and arranged such that said screw may pass therethrough such that it would enter one vertebra anteriorly, pass into and through said disk cage and into the adjacent vertebra to cross-pin said vertebra to said disk cage.

11. The apparatus of claim 10 wherein said disk cage is substantially hollow defining a hollow region and includes a plurality of openings from an exterior surface to the hollow region to allow bone ingrowth through said disk cage.

12. The apparatus of claim 10 wherein said disk cage includes a tool receiving mechanism at the ventral end for receiving an insertion and guiding tool.

13. The apparatus of claim 10 wherein said disk cage includes exterior surface treatments for gripping against a bone surface.

14. The apparatus of claim 10 wherein the distance between said upper and lower surface is greater than the distance between said opposing side surfaces.

15. The apparatus of claim 1 wherein said upper and lower surfaces are generally convex and include a plurality of threads thereon.

16. The apparatus of claim 1 wherein said upper and lower surfaces are not parallel to each other.

17. A method for anteriorly correcting spondylolisthesis comprising the steps of:

(a) exposing adjacent vertebrae and the disk therebetween anteriorly;

(b) reaming out said disk to create and interdiscal space;

(c) lifting and realigning the adjacent vertebra as required;

(d) inserting a disk cage into the interdiscal space to provide a rigid support across the adjacent vertebrae;

(e) drilling an opening through one vertebra, through an angled opening in said disk a cage and into said adjacent vertebra; and (f) inserting an elongated screw through said opening to cross-pin said disk cage to said adjacent vertebrae.

18. A system for fixing and correcting spondylolisthesis anteriorly comprising:

a) an instrument having a pair of linked arms each having a free end and each further having a sharp projection located upon the free end; a slide member supported upon said linked arms and being freely moveable along the length of said linked arms; said slide member having a plurality of push members oriented in the direction opposite to that of the sharp projections; a central rod attached to the linked arms through a central opening and being further attached to the slide member; and a depth adjustment mechanism having the means to fix the position of the slide member along the linked arms;

b) a substantially hollow disk cage having an opening therethrough and a plurality of side holes; said disk cage further having an upper and a lower surface which each contain one or more guide holes;

c) an insertion tool having an elongated body, said elongated body having a head constructed and manufactured to be of determinable size and shape so that said head can fasten to said opening of the disk cage;

d) a drill guide having a means for fastening to the opening of the disk cage; said drill guide further having a hollow shaft mounted to the fastening means so that when the drill guide is properly fastened to the disk cage the hollow shaft will be in linear alignment with the guide holes of the disk cage; and e) an elongated screw constructed and arranged to pass through said guide holes of said disk cage.

19. The system for fixing and correcting spondylolisthesis anteriorly of claim 18 wherein the screw is a threaded screw having a hollow bore and side openings.

20. The system for fixing and correcting spondylolisthesis anteriorly of claim 18 wherein the upper and lower surfaces of the disk cage have a threaded surface treatment.

21. A method of correcting and fixing spondylolisthesis anteriorly comprising:

(a) placing a distracting tool against and between two adjacent vertebrae at the point where said vertebrae are in misalignment;

(b) realigning said vertebrae by utilizing the distraction tool to lift and distract one vertebra from the adjacent vertebra thereby increasing the gap between said vertebrae;

(c) reaming out the disk between said vertebrae to create an interdiscal space;

(d) inserting an insertion device into a disk cage, said disk cage including an angled through guide hole therethrough;

(e) placing the disk cage into the interdiscal space;

(f) aligning said disk cage by placing the guide holes of said disk cage in alignment with the vertebrae surrounding said disk cage;

(g) removing of said insertion device from the disk cage;

(h) removing said distracting tool from said adjacent vertebrae;

(I) mounting a drill guide into said disk cage to position said drill guide to be in linear alignment with said disk cage guide holes;

(j) drilling a hole through said drill guide anteriorly into a vertebra at an angle sufficient to lead a drill bit through the guide hole of the drill cage and into the adjacent vertebra;

(k) removing said drill bit and drill guide from said disk cage; and (l) inserting a screw into the hole running between both vertebra thereby cross-pinning the adjacent vertebrae together through the disk cage and screw.

22. A method of correcting and fixing spondylolisthesis anteriorly comprising:

(a) placing a distracting tool against and between two adjacent vertebrae at the point where said vertebrae are in misalignment;

(b) realigning said vertebrae by utilizing the distraction tool to lift and distract one vertebra from the adjacent vertebra thereby increasing the gap between said vertebrae;

(c) reaming out a disk between said vertebrae to create an interdiscal space;

(d) inserting an insertion device into a disk cage, said disk cage being prismoidal in shape and having a first pair of opposing surfaces that are spaced closer together than a second pair of generally opposing surfaces;

(e) placing the disk cage into said interdiscal space with the first pair of opposing surfaces against said vertebrae;

(f) rotating said disk cage through application of torque to said insertion device until said second pair of opposing surfaces are against said vertebrae to thereby firmly seat said disk cage between said vertebrae;

(g) aligning said disk cage by placing the guide holes of said disk cage in alignment with the vertebrae surrounding said disk cage;

(h) removing of said insertion device from the disk cage;

(I) removing said distracting tool from said adjacent vertebrae;

(j) mounting a drill guide into said disk cage to position said drill guide to be in linear alignment with said disk cage guide holes;

(k) drilling a hole through said drill guide anteriorly into a vertebra at an angle sufficient to lead a drill bit through the guide hole of the drill cage and into the adjacent vertebra;

(l) removing said drill bit and drill guide from said disk cage;

(m) inserting a screw into the hole running between both vertebra thereby cross-pinning the adjacent vertebrae together through the disk cage and screw.

(n) aligning said disk cage thereby placing the guide holes of said disk cage in alignment with the vertebrae surrounding said disk cage;

(o) applying bone ingrowth medium into said disk cage and said hollow screw to thereby encourage formation of bone and fibrous fusions between both vertebra across said disk.

* * * * *

UNITED STATES PATENT AND TRADEMARK OFFICE
CERTIFICATE OF CORRECTION

PATENT NO.    : 6,056,749
DATED         : May 2, 2000
INVENTOR(S)   : Stephen D. Kuslich It is certified that error appears in the above-identified patent and that said Letters Patent is hereby corrected as shown below:

<u>Column 4</u>,
Line 38, replace ";" with --:--;

<u>Column 5</u>,
Line 46, between "disk" and "cage," delete "a".

Signed and Sealed this

Third Day of July, 2001

*Attest:*

*Nicholas P. Godici*

*Attesting Officer*

NICHOLAS P. GODICI
*Acting Director of the United States Patent and Trademark Office*